(12) United States Patent
Barnard et al.

(10) Patent No.: US 9,689,821 B2
(45) Date of Patent: Jun. 27, 2017

(54) CONDUCTIVITY MEASUREMENT CELL

(75) Inventors: Jonathan D. Barnard, Bedford (GB);
Stephen J. Carlisle, Sherington (GB);
Malcolm R. Jones, Harpenden (GB)

(73) Assignee: SPD Swiss Precision Diagnostics GMBH, Geneva (CH)

( * ) Notice: Subject to any disclaimer, the term of this patent is extended or adjusted under 35 U.S.C. 154(b) by 743 days.

(21) Appl. No.: 13/142,561

(22) PCT Filed: Dec. 24, 2009

(86) PCT No.: PCT/GB2009/002958
§ 371 (c)(1),
(2), (4) Date: Aug. 15, 2011

(87) PCT Pub. No.: WO2010/076556
PCT Pub. Date: Jul. 8, 2010

(65) Prior Publication Data
US 2011/0291670 A1    Dec. 1, 2011

(30) Foreign Application Priority Data
Dec. 31, 2008    (GB) .................................. 0823719.0

(51) Int. Cl.
*G01N 21/75* (2006.01)
*G01N 27/07* (2006.01)
(Continued)

(52) U.S. Cl.
CPC ........... *G01N 27/07* (2013.01); *G01N 33/493* (2013.01); *H03K 3/0315* (2013.01)

(58) Field of Classification Search
CPC .. G01N 27/3272; G01N 27/327; G01N 27/26; G01N 27/3271; G01N 33/5438; G01N 17/02; G01N 27/414; G01N 33/48707; G01N 27/3274; G01N 33/48771; G01N 27/07; G01N 33/493; A61B 5/14532; A61B 5/1486; A61B 5/1495;
(Continued)

(56) References Cited

U.S. PATENT DOCUMENTS 3,648,160 A    3/1972 Beaver
4,262,253 A    4/1981 Clark
(Continued)

FOREIGN PATENT DOCUMENTS

EP    0121385    10/1984
EP    1029928    8/2000
(Continued)

OTHER PUBLICATIONS

International Search Report for International Application No. PCT/GB2009/002958 (mailed Jul. 6, 2010).

*Primary Examiner* — Dennis M White
(74) *Attorney, Agent, or Firm* — Klarquist Sparkman, LLP

(57) ABSTRACT

The application relates to a conductivity measurement cell for measuring the concentration of a preselected biomarker or analyte in a body fluid, such as urine. In order to reduce the effect of sample dilution on measured concentration, the measured concentration can be normalized by a dilution factor, which can be determined from electrical conductivity. A test strip and measurement apparatus is disclosed for performing such normalized concentration measurement.

15 Claims, 11 Drawing Sheets

(51) Int. Cl.
  *H03K 3/03* (2006.01)
  *G01N 33/493* (2006.01)

(58) Field of Classification Search
  CPC .... A61B 2560/0252; A61B 2560/0223; A61B
       2562/227; C12Q 1/001; C12Q 1/006;
       C12Q 1/00; C12Q 1/002; C12Q 1/54;
       C12Q 1/68; H03K 3/0315
  USPC ....... 422/52, 73, 82.01, 82.05, 82.08, 82.09,
       422/82.11, 99, 102, 400, 401, 420, 421,
       422/422, 423, 424, 425, 426, 427, 428,
       422/429, 68.1, 82.06, 407, 501, 502, 503,
       422/504; 436/164, 177, 43, 63; 435/29,
       435/4, 6, 7.1
  See application file for complete search history.

(56) References Cited

U.S. PATENT DOCUMENTS

| | | | |
|---|---|---|---|
| 4,511,845 A | | 4/1985 | Dauphinee et al. |
| 4,673,869 A | | 6/1987 | Michael |
| 4,713,165 A | * | 12/1987 | Conover et al. ......... 204/403.05 |
| 4,897,173 A | * | 1/1990 | Nankai et al. ........... 204/403.05 |
| 5,120,420 A | | 6/1992 | Nankai et al. |
| 5,148,125 A | | 9/1992 | Woodhead et al. |
| 5,229,282 A | * | 7/1993 | Yoshioka et al. ............. 435/177 |
| 5,264,103 A | | 11/1993 | Yosioka et al. |
| 5,997,817 A | * | 12/1999 | Crismore et al. .......... 204/403.1 |
| 7,563,588 B2 | * | 7/2009 | Gao et al. ...................... 435/14 |
| 2002/0067174 A1 | | 6/2002 | McAllister |
| 2005/0273293 A1 | | 12/2005 | Howe |
| 2006/0105467 A1 | | 5/2006 | Niksa et al. |

FOREIGN PATENT DOCUMENTS

| | | | |
|---|---|---|---|
| EP | 1380837 | | 1/2004 |
| EP | 1577668 | | 9/2005 |
| GB | 1318815 | | 5/1973 |
| GB | 2019010 | | 10/1979 |
| GB | 2069702 | | 8/1981 |
| JP | 58191942 | | 11/1983 |
| JP | 63314912 | | 12/1988 |
| JP | 3130653 | | 6/1991 |
| JP | 2004226358 A | * | 8/2004 |
| JP | 2006191262 | | 7/2006 |
| WO | WO 9725615 | | 7/1997 |
| WO | WO 9947907 A1 | * | 9/1999 |
| WO | WO 2008/076212 | | 6/2008 |

* cited by examiner

CONDUCTIVITY MEASUREMENT CELL

CROSS REFERENCE TO RELATED APPLICATIONS

This is the U.S. National Stage of International Application No. PCT/GB2009/002958, filed Dec. 24, 2009, which was published in English under PCT Article 21(2), which in turn claims priority from Great Britain Application No. 0823719.0, filed Dec. 31, 2008.

FIELD OF INVENTION

The present application relates to a conductivity measurement cell.

BACKGROUND OF INVENTION

It can be useful to measure the concentration of a preselected biomarker, or analyte, in a body-fluid such as urine. However, depending on the level of hydration of the patient, urine may be relatively dilute or concentrated and this variability in urine dilution can substantially affect the measured analyte concentration, preventing accurate diagnosis. In order to reduce the effect of the variability of urine sample dilution on the measured analyte concentration, the measured analyte concentration can be normalised by the urine dilution factor, which can be determined from its electrical conductivity.

Electrical conductivity, hereafter referred to as conductivity, is a physical property of materials. The conductivity of a particular material is usually temperature dependent and is therefore usually quoted at 25 degrees Celsius. The conductivity of a given material at 25 degrees Celsius will be referred to as the material's temperature corrected conductivity.

The conductance of a given sample of a given material is related to the conductivity of the material by the length and cross sectional area of the material sample. Conductivity is expressed in Siemens/cm. Conductance is expressed in Siemens and is the inverse of resistance.

US 2006/0073606 A1 discloses a urine analyser which determines urine dilution by measuring the level of creatinine (a coloured substance) by optical colorimitry, and corrects an analyte (in this case, albumin, a protein, which is indicative of kidney disease) concentration measurement with the urine dilution factor. However, the apparatus required for measuring creatinine concentration by optical means is cumbersome and expensive. The analyser relies upon a temperature controller having a heater and thermistor, is bulky, power hungry and unsuitable for adapting to a hand held disposable assay device.

WO 2006/087697 A2 discloses a method of measuring urine dilution by measuring the electrical conductivity of the urine sample. The electrical conductivity of urine is known to be related to its dilution. A measured analyte concentration (in this case, thromboxane, which is indicative of heart disease) is then corrected using the measured electrical conductivity. However, electrical conductivity of a sample is known to vary with sample temperature, therefore a temperature dependent error exists in the corrected analyte concentration result.

In a related area it is also known that the hematocrit, or packed cell volume, of a blood sample is related to the electrical conductivity of the sample. The conductivity of blood varies by about 2% per degree Celcius. U.S. Pat. No. 3,648,160 discloses an apparatus which comprises two conductivity cells, each having a pair of electrodes, and analogue signal processing means for correcting a measure of blood sample conductivity using a measure of conductivity of a reference blood plasma which has had the blood cells removed. The disclosure is unsuitable for use in a convenient point of care device, such as a disposable assay device, since its features render it relatively expensive and unsuitable for interfacing to a microprocessor. The disclosed device is also susceptible to errors in temperature compensation if the blood sample and the reference are not maintained at the same temperature as each other. In addition, the performance of the apparatus changes over time requiring repeated calibration against a known standard.

BRIEF DESCRIPTION OF THE INVENTION

The invention is set out in the claims.

As a result of the features set out a number of advantages are available. By deriving temperature relying on inherent, reference and sample conductance the temperature measure can be obtained quickly and accurately. In order to compensate full temperature variation during the measurement process, conductance can be repeatedly measured and the temperature derived when successive ratio calculations differ by less than an error amount meaning that the temperature has settled. By providing a membrane between the sample and reference, the temperature can be matched rapidly. By providing shared electrodes in parallel across the referencing sample the number of components required can be minimised enabling a simplified circuit with two electrodes. By using individual meters and test strips these can be individually calibrated prior to carrying out a test enabling any variation in manufacture between respective test strips and meters to be compensated for.

Embodiments of the invention will now be described in detail with reference to the attached Figures.

FIGURES

DETAILED DESCRIPTION

In order to calculate temperature corrected conductivity, two measurements are commonly required; conductivity (uncorrected for temperature) and the temperature at which the uncorrected conductivity was measured. A significant proportion of the cost associated with devices for measuring temperature corrected conductivity can be attributed to the extra components required for the accurate measurement of temperature. Significant cost savings can result if the need to measure temperature is eliminated. The present invention compensates for temperature without measuring temperature, and neither does it require the use of an on-board reference of known conductivity in order to calculate temperature.

The present invention provides increased accuracy over known devices which measure conductivity but do not correct for temperature. The present invention also improves over known methods of compensating for temperature variability in conductivity measurements without measuring temperature, and more specifically provides savings in cost and increases in accuracy, by reducing component count, and by improving temperature matching between the sample being measured and the temperature compensating reference. An example operating temperature range for the invention is between 10 and 40 degrees Celsius.

Figure 1:
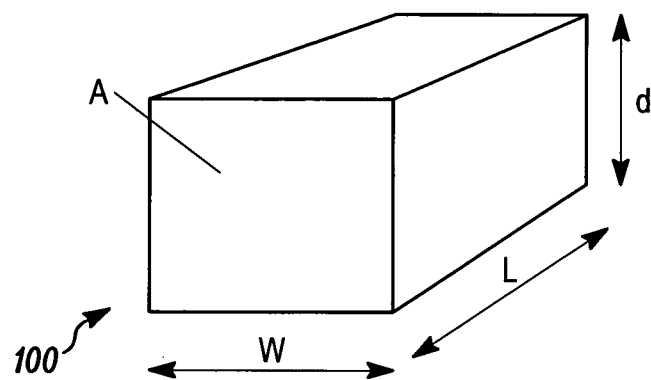
FIG. 1 shows schematically a substance having a conductivity.

FIG. 1 shows a sample of material with length L, and cross sectional area A (defined by width W and depth d). The dimensions are relevant to measurement of the properties as discussed in more detail below.

Figure 2:
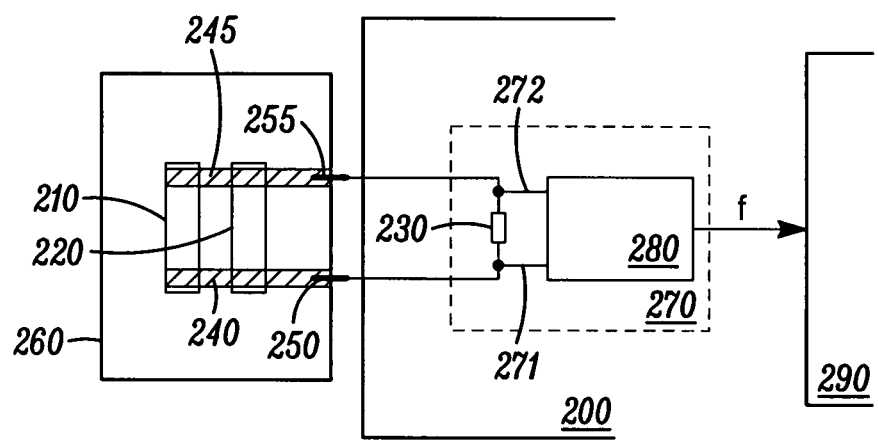
FIG. 2 shows a conductivity measurement test strip connected to a conductivity measuring device comprising an electronic circuit for generating a frequency output.

As shown in FIG. 2, the present invention is designed around a conductivity measurement test strip (260). In an embodiment, the test strip (260) incorporates two containers (otherwise herein referred to as cells). A first cell (210), called a sample cell, preferably comprises a container suitable for containing a sample or sample fluid (for example a liquid, or suspension) and means (such as a hole) for filling it. A second cell (220), called a reference cell, comprises a container suitable for containing a reference or reference material (which can be a solid, fluid, liquid, gel, powder or an electrical component). The reference (for example, KCl-potassium chloride solution) has a known conductivity and a similar coefficient of temperature induced conductivity variation to that of the sample fluid. The reference can be sealed into the reference cell (220) during manufacture, or means for filling it when in use can be provided, such as a reference introduction hole (345).

A pair of spaced electrodes (240, 245), extend into both the sample cell (210) and into the reference cell (220). The electrodes (240, 245) are arranged such that an electrically conductive portion of each electrode (240, 245) acts as a node exposed within both the sample cell (210) and the reference cell (220). The electrodes connect the two cells electrically in parallel. Thus, the electrodes (240, 245) are shared by the sample cell (210) and the reference cell (220). Each electrode is provided with an electrode connection point (250, 255) for connecting to the first and second nodes (271, 272) of a measurement means (270) of a device for deriving a temperature corrected measure of electrical conductivity (200). Thus, there is provided a simple two-wire interface between the test strip (260) and the measurement means (270).

Optionally, the measurement means can incorporate a third node (273) (described with reference to FIG. 12 below) to which a third electrode of the test strip (260) can connect. In such embodiments, the second electrode (240) is shared by the sample cell (210) and the reference cell (220), and the first electrode (245) and third electrode are dedicated to each of the sample cell (210) and reference cell (220).

The device (200) comprises measurement means (270), such as a meter, the measurement means (270) comprising a first, inherent conductance (230) (so named because it is inherently a part of the measurement means) and an electronic circuit (280) arranged for generating a frequency output (f), the frequency output (f) having a frequency which is related to a conductance between a first node (271) and a second node (272).

The frequency output (f) is preferably fed into a microcontroller (290), which can incorporate indicating means such as a display or an LED, and can incorporate control input means such as a switch or a keyboard.

Figure 3:
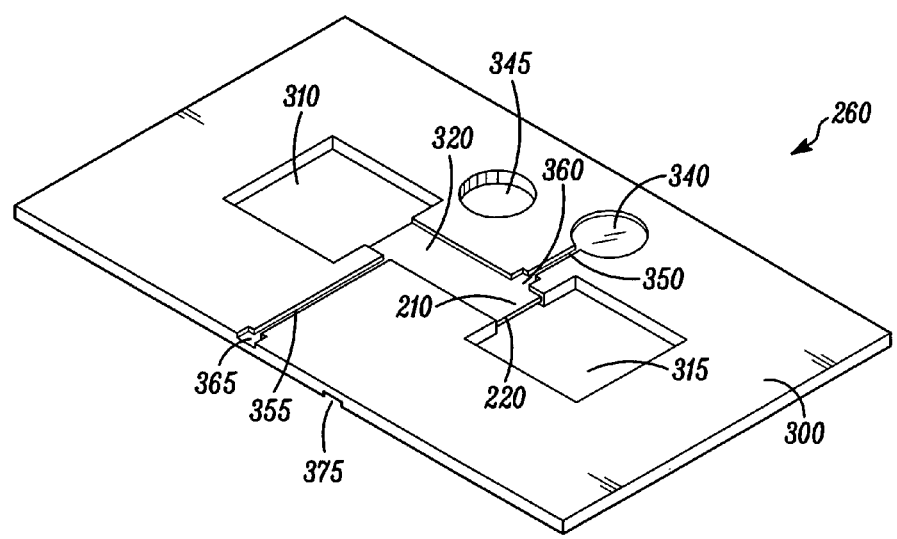
FIG. 3 shows a body of a conductivity measurement test strip.

As shown in FIG. 3, the diagnostic or conductivity measurement test strip (260) comprises a body (300), two locations for electrodes (310, 315), a sample container (210) and a reference container (220). In the embodiment shown, the sample container (210) and the reference container (220) are separated by a coincident membrane (320). The sample container is associated with a sample application zone comprising a sample introduction hole (340) and this hole (340) is fluidically connected to the sample container (210) by a capillary feed tube (350). A capillary drain tube (355) leads from the sample container (210) to the atmosphere and is terminated by a capillary break (365). In some embodiments, the reference container (220) is associated with a reference introduction hole (345). In other embodiments, the reference material is sealed in the reference container (220) and there is no reference introduction hole (345).

Figure 4:
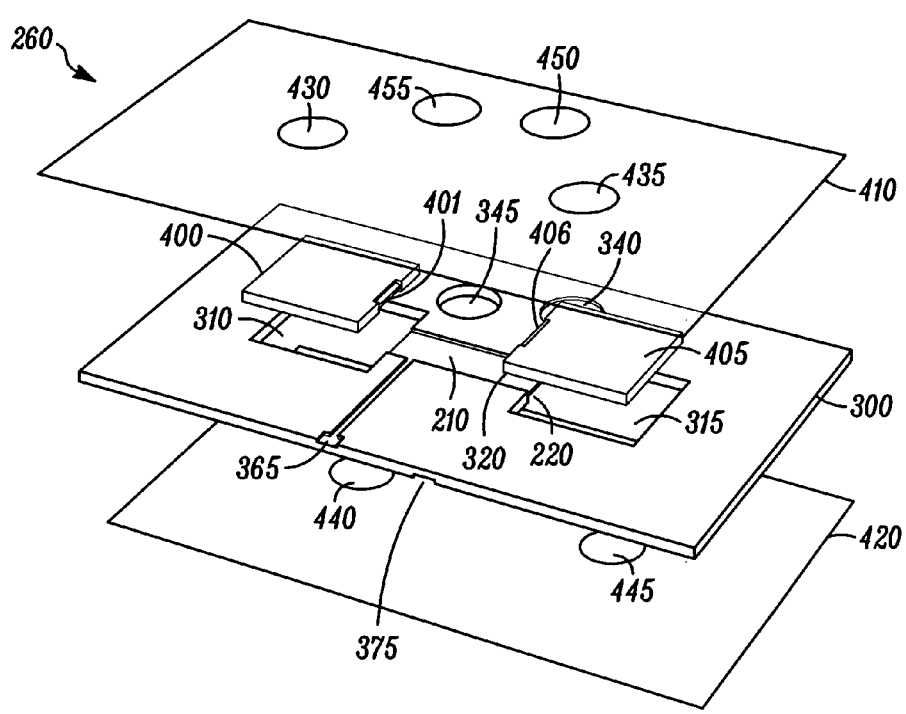
FIG. 4 and FIG. 5 show the component parts of a conductivity measurement test strip.
Figure 5:
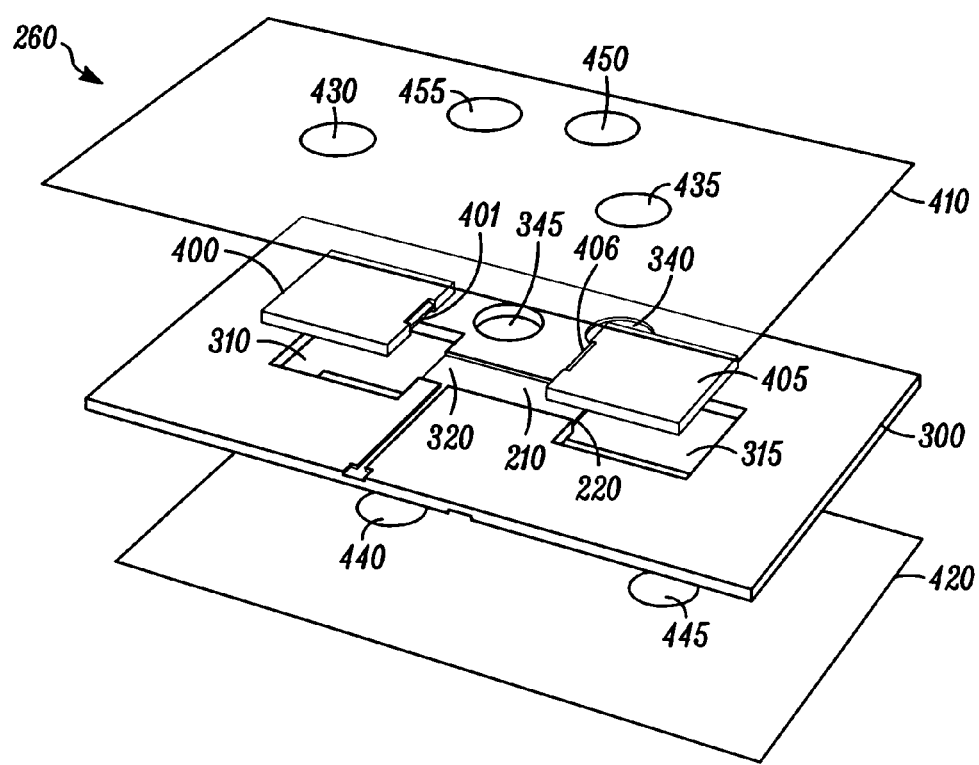

FIGS. 4 and 5 show an exploded view of the main components of the conductivity measurement test strip (260). The first and second electrodes (400, 405) are arranged in the electrode locations (310, 315), and can incorporate chamfers (401, 406) on the edge which is coincident with the sample container (210) and reference container (220). Sealing sheets (410,420) are bonded to the body (300). Each sealing sheet comprises electrode connection holes (430, 435, 440, 445). The upper sealing sheet (410) also comprises a sample introduction access hole (450) and can comprise a reference introduction access hole (455). The positioning of the containers in a sandwich configuration allows the use of two electrodes to measure the conductivity of both reference and sample. This saves cost over using two cells mounted side by side, which would require at least 3 electrodes and connective pathways.

Figure 6:
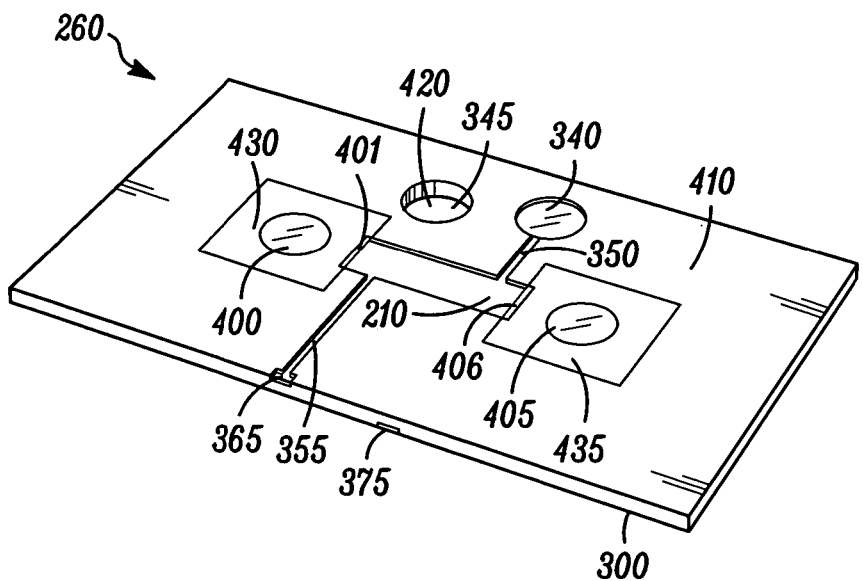
FIG. 6 shows an assembled conductivity measurement test strip.

FIG. 6 shows the assembled conductivity measurement test strip (260). As shown, the lower sealing sheet (420) seals the bottom of the reference introduction hole (345). The electrode chamfers (401, 406) can be seen in this Figure. The electrodes (400, 405) comprise the ends of the sample container (210) and of the reference container (220).

Figure 7:
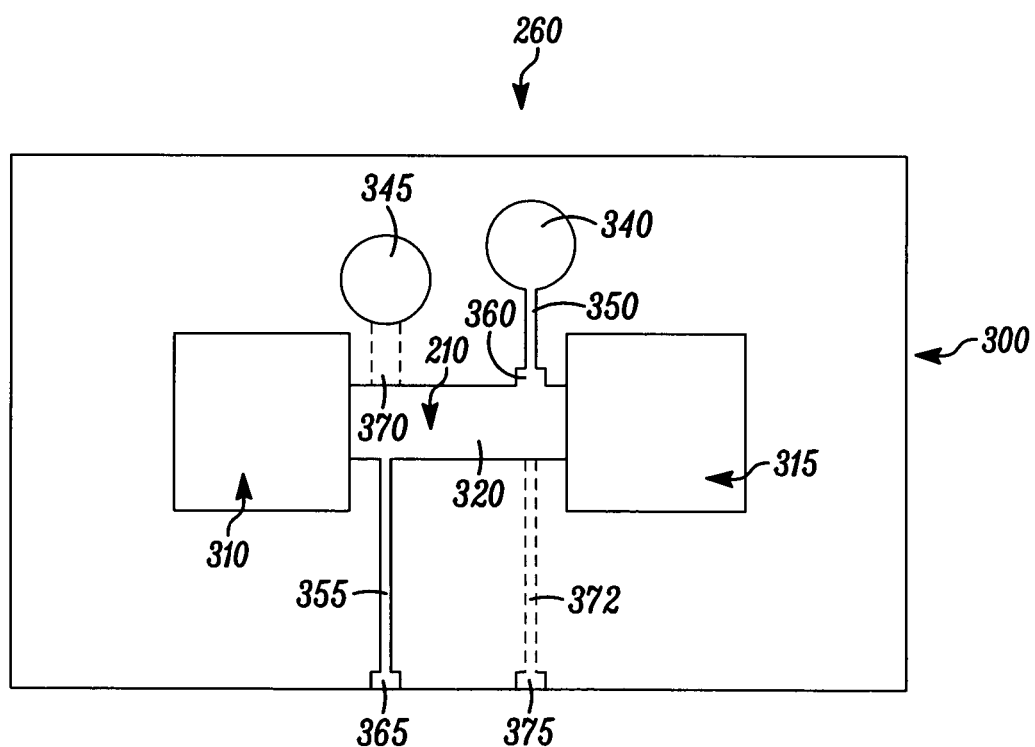
FIG. 7 is a plan view of a conductivity measurement test strip, showing features on the underside of the test strip.

FIG. 7 shows in plan view the conductivity measurement test strip. The reference introduction hole (345) is connected to the reference container (220) by a reference capillary feed tube (370), and the reference container (220) is connected to the atmosphere by a reference capillary drain tube (372). The reference capillary drain tube (372) is terminated at the atmosphere side by a capillary break (375).

Figure 8:
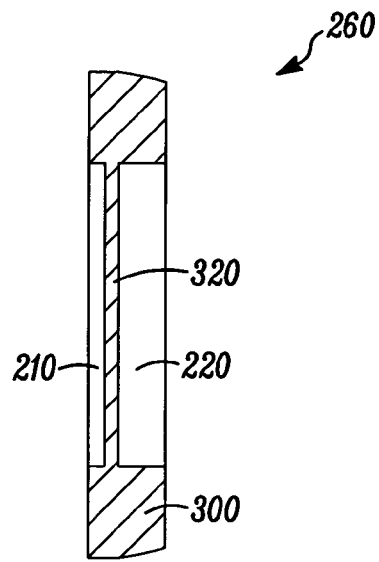
FIG. 8 is a cross-sectional view through a central vertical line through FIG. 7.

FIG. 8 shows a sectional view through the body (300) of the conductivity measurement test strip (260). The sample container (210) is separated from the reference container (220) by a membrane (320).

Figure 9:
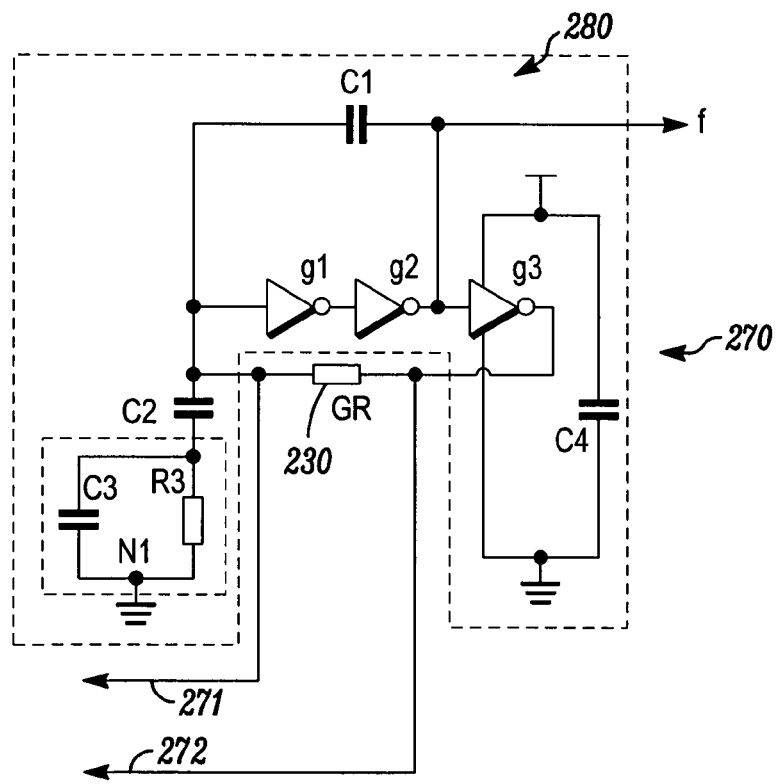
FIG. 9 is a circuit diagram of an electrical circuit for generating a frequency output which is related to a conductance.

FIG. 9 shows an electronic circuit suitable for use in the measurement means (270) and which produces a frequency output (f) having a frequency which is related to the conductance between first and second nodes (271, 272). Three CMOS or low voltage CMOS inverter logic gates (g1, g2, g3) are arranged in series, with the first inverter output feeding the second inverter input, and the second inverter output feeding the third inverter input. The first inverter input is connected to a first terminal of the conductance (230) and to a first node (271). The third inverter output is connected to the second node (272) and to a second terminal of a conductance (230). A first capacitor (C1) connects the second inverter output to the first inverter input. A second capacitor (C2) connects the first inverter input towards ground, and optionally either to ground or to a network (N1) which is connected to ground. The network N1 preferably comprises a third capacitor (C3) and resistor (R3) in parallel. The frequency output (f) is connected to the second inverter output. A fourth capacitor (C4) is connected between the power supply and ground. When power is removed, the circuit ceases to operate and draws negligible current from the power source.

In overview, when in use, the electrodes (240, 245) connect the reference (220) and the sample (210) electrically in parallel. The electrode connection points (250, 255) allow connection and disconnection of the test strip with the measurement means at the first and second nodes (271, 272) or the measurement means (270). This can be by virtue of relative physical movement bringing the electrical parts into electrical connection. Alternatively the arrangement can be ready assembled or integral, and electrical connection made by virtue of electrically or electronically switching the various components into the circuit.

The circuit (280) of the measurement means (270) continuously outputs a signal (f) having a frequency which is proportional to the parallel (total or aggregate) conductance between the first node (271) and the second node (272). The output signal (f) is preferably a digital signal with 1 bit resolution and is thus suitable for directly inputting to a microcontroller (290) without the need for an expensive Analogue to Digital Converter (ADC).

In operation a first measurement (f1) is taken with the test strip (260) disconnected from the measurement means (270) to obtain a measure of the first, inherent conductance. Alternatively the measure of conductance can be obtained or stored during a calibration or storage stage, and the measure obtained by retrieving the stored value.

The reference is sealed into the reference cell during manufacture, or can be introduced into the reference cell (220) via the reference introduction hole (345). A second measurement (f2) is taken with the test strip (260) connected to the measurement means (270) and with the reference present in the reference cell (220) and with the sample cell (210) empty to obtain a measure of the second conductance.

A sample is then introduced into the sample cell (210), preferably via the sample introduction hole (340). The action of the capillary feed tube (350) and capillary drain tube (355) aids the complete filling of the sample cell (210) when a sample is applied to the sample introduction hole (340). A third measurement (f3) is taken with the test strip (260) connected to the measurement means (270) and with the reference present in the reference cell (220) and with the sample cell (210) filled with a sample fluid to obtain a measure of the third conductance.

Although the above example sets out the three measurements (f1, f2, f3) being taken in the order f1, f2, f3, the measurements can be taken in any order and/or can be repeatedly taken and optionally averaged.

A microcontroller calculates the conductivity of the sample from first, second and third measurements (f1, f2, f3) of the frequency output (f). The microcontroller can incorporate a display or indicator (such a Light Emitting Diode) which it can use to direct a user to connect the test strip (260) to the measurement means (270), to disconnect the test strip (260) from the measurement means (270), to introduce a sample into the sample container (210) or other actions as necessary. The microcontroller can optionally detect the attachment of the test strip (260) or the introduction of the sample into the sample container (210) by the change in frequency of the frequency output (f).

The frequency of the circuit (280) output signal (f) is given by:

$$f = \alpha \times G$$

Where $\alpha$ is the interface gain term, which is dependent on the circuit (280) design, and G is:
1. $G=G_R$ The conductance of the interface circuit (280) when the test strip is not connected (termed the "first, or inherent conductance" of the circuit).
2. $G=G_R+G_{ref}$ The parallel conductance when the test strip is connected but no sample is present (the "second conductance").
3. $G=G_R+G_{ref}+G_M$ The parallel conductance when the test strip is connected and a sample is present (the "third conductance").

The sample cell and reference cell conductances are given by:

$$G_M = \frac{\sigma_{M@25}}{\theta_M} \times \beta_M(T)$$

and $$G_{ref} = \frac{\sigma_{ref@25}}{\theta_{ref}} \times \beta_{ref}(T)$$

Where $\theta_M$ and $\theta_{ref}$ are the cell constants of the sample cell and the reference cell respectively (which are related to the cell dimensions), $\beta_M(T)$ and $\beta_{ref}(T)$ are the temperature coefficients, $\sigma_{M@25}$ is the conductivity of the sample at 25 degrees Celsius and $\sigma_{ref@25}$ is the conductivity of the reference at 25 degrees Celsius. The reference is selected so that its temperature coefficient matches, as closely as possible, that of the sample, that is $\beta_M(T)=\beta_{ref}(T)$.

If the temperature of the sample cell (210) and the reference cell (220) are the same then the $\beta(T)$ terms, in the ratio of sample cell conductance $G_M$ to reference cell conductance $G_{ref}$ cancel giving the following equation for the sample conductivity at 25° C. in terms of the known reference conductivity at 25° C. which is independent of measurement temperature.

$$\sigma_{M@25} = \frac{G_M \times \theta_M}{G_{ref} \times \theta_{ref}} \times \sigma_{ref@25}$$

$G_M$ and Gref are measured while the ratio of cell constants is known from the test strip design.

The ratio of sample conductance to reference conductance can be found in terms of the frequency output measurements (f1, f2, f3) as follows:

$$\sigma_{M@25} = \left(\frac{f3-f2}{f2-f1}\right) \times \frac{\theta_M}{\theta_{ref}} \times \sigma_{ref@25}$$

Where f1 is the frequency measured before the strip is connected, f2 is the frequency measured with the strip connected but no sample present, and f3 is the frequency measured with the sample added. Since this is a ratiometric measurement the exact value of the interface gain term α is not important so long as it is constant and is not a function of conductance.

If the sample cell (210) and reference cell (220) constants are equal then the cell constant ratio term disappears. In practice it is more likely that the cell constants will be different so that the full dynamic range of the interface circuit (280) can be utilised. Any cell dimension errors that are common to both cells are rejected by the cell constant ratio. Since the reference conductivity and cell constants are known, the sample conductivity can be calculated from the three frequency measurements f1, f2, f3.

A sample can be introduced into the sample introduction hole (340) shown in FIG. 3 by a user, or by equipment under the control of the microcontroller. The sample, which is preferably a liquid, is drawn through the capillary feed tube (350) by capillary action and into the sample container (210). As the sample passes through the capillary feed tube (350), it is brought to substantially the same temperature as the test strip (260) and the reference, due to the relatively high ratio of surface area of the capillary feed tube (350) to the volume of the capillary feed tube (350).

It is important that the sample and reference are brought to and maintained at the same temperature before and during measurement, otherwise the temperature coefficient terms of the equation described previously, β(T), will not be cancelled completely. An example case in use is with the test strip (260) at room temperature and the sample at body temperature. The reference will be at the same temperature as the test strip (260), having either been sealed into the test strip (260) during manufacture of the test strip (260), or having been introduced to the test strip (260) earlier and having been given time to reach temperature equilibrium with the test strip (260). The test strip (260) is designed to rapidly make convergent the sample and test strip (260) temperatures. This is achieved by the following features:

1. The surface area to volume ratio of the sample cell (210) is maximised so that the sample can rapidly reach the temperature of the test strip (260).
2. The thermal resistance between the sample cell (210) and the reference cell (220) is minimised by the two cells (or containers) (210, 220) sharing a base area. The sample cell (210) and reference cell (220) have either the same base area, or the base area of the sample cell (210) can be smaller than the reference cell (220) area. The two cells (210, 220) are positioned in the test strip (260) such that in plan view the cell base areas are coincident and/or overlapping. The cells (210, 220) are separated by a membrane (320) which is typically moulded as part of the cell body (300) and is typically less than 1 mm thick to further minimise the thermal resistance between the cells.
3. The thermal mass of the sample is small compared to the thermal mass of the test strip (260). This is achieved by minimising the sample volume.
4. The temperature of the sample is further brought closer to the temperature of the test strip (260) (and therefore to the temperature of the reference) by passing the sample through a capillary feed tube (350). The capillary feed tube (350) is of a sufficient length to ensure the sample fluid has as much time as possible to assume the temperature of the test strip (260) and therefore also the temperature of the reference.

As the sample is drawn into the sample container (210) by capillary action, it fills the sample container (210) and expels air from the sample container (210) which exits via the capillary drain tube (355). When the sample reaches the capillary drain tube (355), the sample is drawn down the capillary drain tube (355) until it reaches the capillary break (365) whereupon capillary action ceases. The sample container (210) is thus completely filled with sample fluid. A similar principle applies when the reference container (220) is filled in use. When the reference container is pre-filled and sealed during manufacture, no such reference filling procedure is necessary in use. As a result a rapid conductivity measurement is available without the requirement for a temperature sensor.

Figure 12:
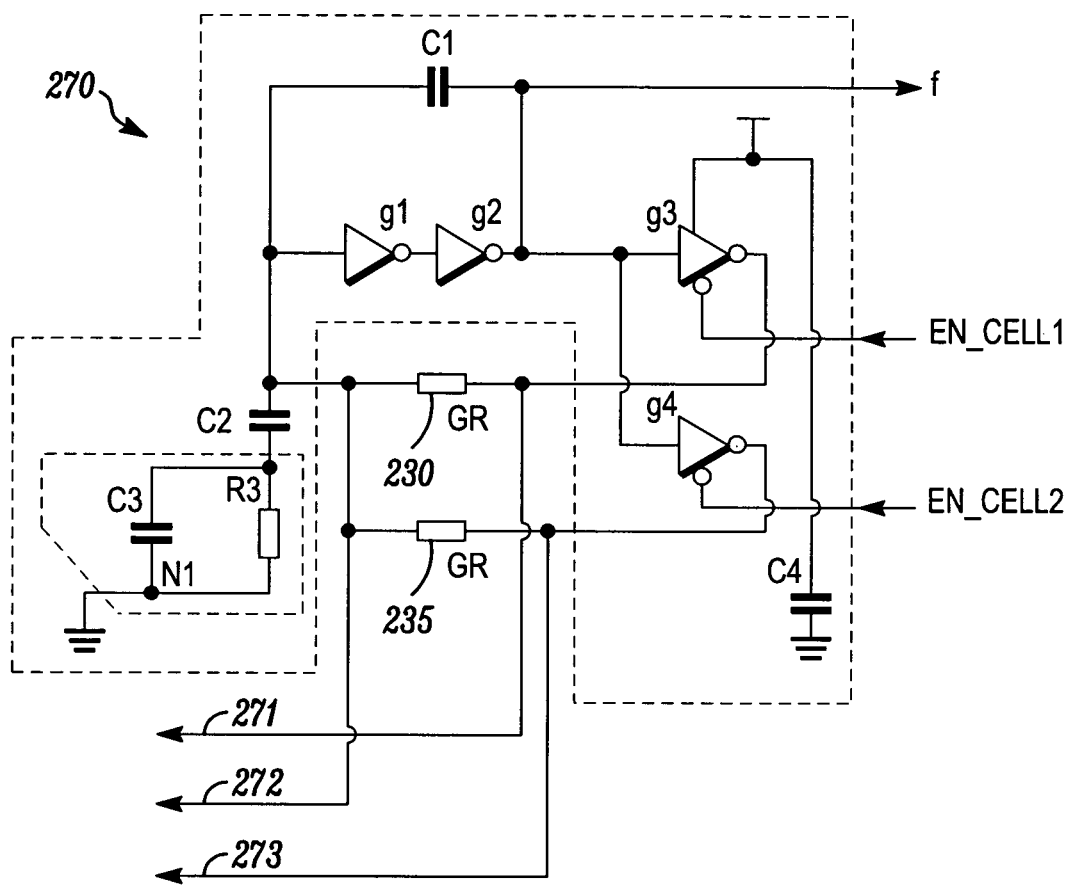
FIG. 12 is a circuit diagram of an electrical circuit for generating a frequency output which is related to a conductance, further incorporating multiple tri-stateable inverters.

FIG. 12 shows a variation on the electronic circuit of FIG. 9, where the third inverter (g3) is of the type comprising a tri-stateable output, that is an output which can be driven to logic 0, driven to logic 1, or un-driven (high impedance). A fourth inverter having a tri-stateable output (g4) can be incorporated in the circuit, and the fourth inverter output connected to a second terminal of a second conductance (235) and to a third node (273), the first terminal of the second conductance (235) being connected to the first inverter input and to the second node (272). Using the circuit of FIG. 12, more than one test strip (260) can be connected and selected between using the tri-state enable inputs to the tri-stateable inverters (EN_CELL1, EN_CELL2). Alternatively, a test strip having two cells and three electrodes, one electrode common to both cells and connected to the second node (272), and each of the other two electrodes dedicated to each of the cells and connected to the first node (271) and third node (273), can be employed. Using this arrangement, it is possible to selectively measure the conductivity of one or other of the cells under control of the tri-state control inputs (EN_CELL1, EN_CELL2).

Figure 13:
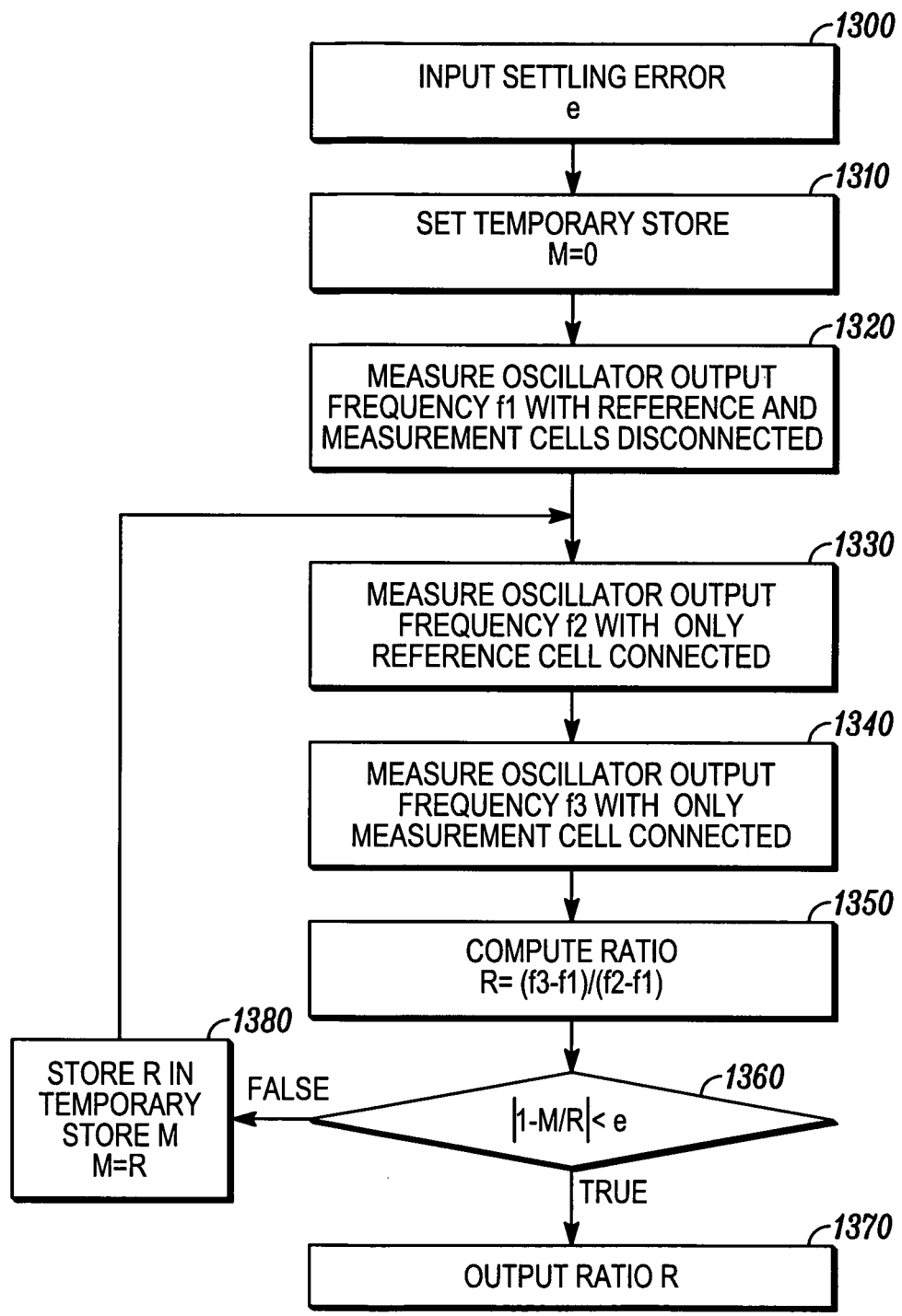
FIG. 13 is a flow chart showing a method of deriving a ratio R for use in deriving a temperature corrected measure of electrical conductivity, incorporating iterative measurement steps.

A variation on the method of taking three frequency measurements (f1, f2, f3) follows and is illustrated in FIG. 13. At step 1300, a settling error, e, is determined, for example by being copied from a memory store or being inputted by a user. At step 1310 a temporary store, M, is zeroed. At step 1320, a first measurement (f1) of the frequency output (f) is taken with the reference and sample cells (220, 210) disconnected. At step 1330, a measurement (f2) of the frequency output (f) is taken with only the reference cell connected. This is conveniently done using the circuit of FIG. 12 and selecting one only of the tri-state enable controls (EN_CELL1, EN_CELL2). At step 1340, a measurement (f3) of the frequency output (f) is taken with only the sample cell connected. Again this is conveniently done using the circuit of FIG. 12 and selecting one only of the tri-state enable controls (EN_CELL1, EN_CELL2). At step 1350, the ratio R=(f3−f1)/(f2−f1) is calculated. At step 1360 the calculation |1−M/R| is evaluated and compared with the settling error, e. If the result is greater than or equal to the settling error, e, then the ratio, R, is stored in the temporary store, M, and the steps from step 1330 to 1360 are iterated. If the result is smaller than the settling error, e, then the ratio, R, is outputted from the method and can be further used to calculate the conductivity of the sample.

Note if the temperature of the strip is stable the ratio R is equivalent to the ratio of the first method.

The iterative method above reduces errors due to temperature settling of the sample after it is introduced to the test strip (260). As the temperatures of the sample and the reference equalise, the result of the calculation |1−M/R| tends towards zero.

In use, the test strip (260) can be connected to the first and second nodes (271, 272) of the measurement means (270) through the electrode connection holes (430, 435). The test strip (260) can be slid into and out of connection with contacts associated with the measurement means, or removably connected in other known ways.

In use, the electronic circuit (280) of FIG. 9 oscillates such that the frequency output (f) continuously switches between a logic '1' and a logic '0' state. The frequency of this oscillation depends upon the value of the conductance (230) and the capacitance of first and second capacitors (C1, C2) and is substantially proportional to the parallel combination of conductances between the first node (271) and the second node (272). The three-gate circuit chosen reduces jitter when compared to a circuit comprising only two gates. The three inverting gate topology applies positive feedback through the first capacitor (C1) before negative feedback is applied via the circuit conductance (230). This generates clean, low jitter, switching transitions.

The fixed, or inherent, circuit conductance (230) enables the circuit to oscillate without a conductivity measurement test strip (260) connected to the measurement means (270). This allows the oscillator to settle and allows a microcontroller to perform self-tests on the oscillator before a test strip (260) is connected.

The inherent conductance (230) also provides a direct current path to the input of the first inverter (g1) to enable biasing of the input. This is necessary because the sample and reference cells become polarised if a non-alternating (d.c.) voltage was applied across them, at which point they would cease to conduct direct current. The cells cannot therefore provide a d.c. path and the inherent conductance (230) provides this instead. By virtue of the oscillator continually reversing the direction of the voltage between the first and second nodes (271, 272), an alternating voltage (a.c.) is applied across the cells (210, 220), further aiding the prevention of cell polarisation.

To consider how the circuit operates, and in particular its special features, it is helpful to consider a point in time when the input to the first inverter (g1) is rising past its switching threshold point (Vt), which is about half the power supply voltage. As the first inverter (g1) switches, the second inverter (g2) output shortly switches from 0V to the power supply voltage. The right hand plate of the first capacitor (C1) begins to charge to the power supply voltage Vs, and as it does so its left hand plate which is connected to the input of the first inverter (g1) also rises in voltage. Since this terminal is already at the threshold voltage Vt (about half the supply voltage), the input to the first inverter would rise above the supply rail (to about Vs+Vt) if it were not for the second capacitor (C2) which acts as a potential divider towards ground. The second capacitor (C2) divides the voltage at the input of the first inverter (g1) thus preventing it from exceeding the supply voltage. Similarly when the voltage at the input of inverter (g1) is falling, capacitor (C2) prevents the voltage falling below 0V.

It is important that the voltage at the input to the first inverter (g1) does not rise above the power supply rail voltage or fall below the 0V rail because most CMOS gates incorporate reverse biased diodes on their inputs and outputs. These diodes are typically connected from ground to the input and from the input to the power supply rail. The same arrangement is also usually present on the gate outputs. Normally, these diodes never conduct because the power supply rail is always at a higher voltage than the input and the input is always at a higher voltage than ground. However in such an oscillator circuit as in FIG. 9, if the second capacitor (C2) were not present (as in prior art oscillators) then the voltage at the input of the first inverter (g1) would periodically rise about the power supply rail voltage due to the charge pumping effect of the first capacitor (C1). In such prior art oscillators, the CMOS input protection diodes would conduct, wasting power by allowing large currents to flow and adversely affecting circuit linearity. In order to prevent circuit linearity being adversely affected, prior art oscillators usually incorporate a resistor in series with the input of the first inverter (g1) so as to limit the current flowing into and out of the first inverter (g1) input, however this resistor would adversely affect jitter by increasing the impedance in series with the input of the first inverter (g1) and would reduce the linearity of the circuit in response to the conductance between the first (271) and second nodes (272). The second capacitor (C2) of the present invention allows the removal of this series resistor used by prior art oscillators. This allows the conductance (230) to be directly connected to the input of the first inverter (g1), increasing the sensitivity and accuracy of the conversion of conductance to a frequency output (f) by the circuit (280).

Furthermore this allows the possibility of replacing the third inverter (g3) with an inverter having a tri-stateable output as shown in FIG. 12. Without the second capacitor (C2), the arrangement of FIG. 12 would not be possible because the output protection diodes of the disabled third or fourth tri-stateable inverters (g3, g4) would periodically conduct and would affect the accuracy of the frequency output (f).

Although CMOS logic gates are specifically mentioned, this aspect of the invention will provide advantages in conjunction with any logic gate family which has approximately symmetrical switching thresholds, and incorporates input or output protection diodes, for example Low voltage CMOS (LVCMOS) or any CMOS family of gates.

Ideally, the gate (g3) output impedance should be less than 1% of the inherent conductance (230).

In use, the nominal output frequency (f) of the circuit is determined as follows:

$$f = \frac{G}{2C Log_e(2K+1)}$$

Where G is the total circuit conductance, C=C1+C2 and $$K = \frac{C1}{C1+C2}.$$

The nominal interface gain is therefore given by $$\alpha = \frac{1}{2C Log_e(2K+1)}.$$

Capacitance C=C1+C2 is selected to optimise the performance of the circuit for a given range of possible conductances between first node (271) and second node (272). With only the inherent conductance (230) present in the circuit (for example when no test strip is connected), the selected value of capacitance will produce a nominal oscillation frequency. If the nominal frequency is too low then the circuit will suffer from increased jitter (Jitter is the uncertainty in the timing of transitions in the oscillator output signal). This results because the signal at the input to the first inverter (g1) passes through the threshold voltage slowly and therefore is susceptible to noise.

Conversely, if the nominal frequency is too high, the propagation delays of the inverter gates (g1, g2, g3) become significant and introduce error, degrading circuit linearity.

Figure 10:
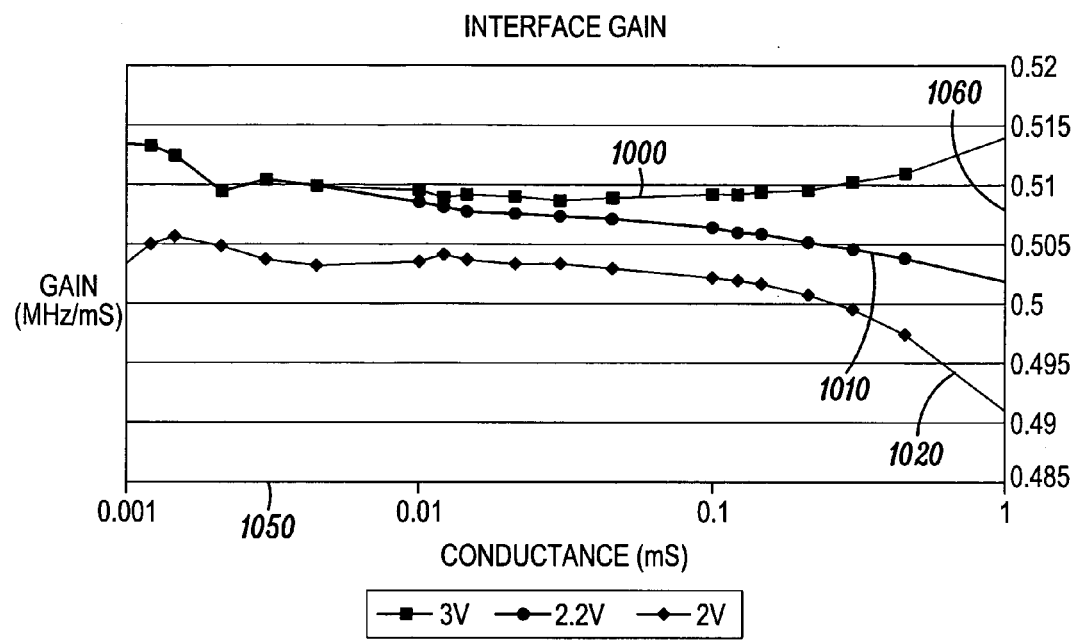
FIG. 10 is a graph of gain versus conductance for a circuit similar to that shown in FIG. 9
Figure 11:
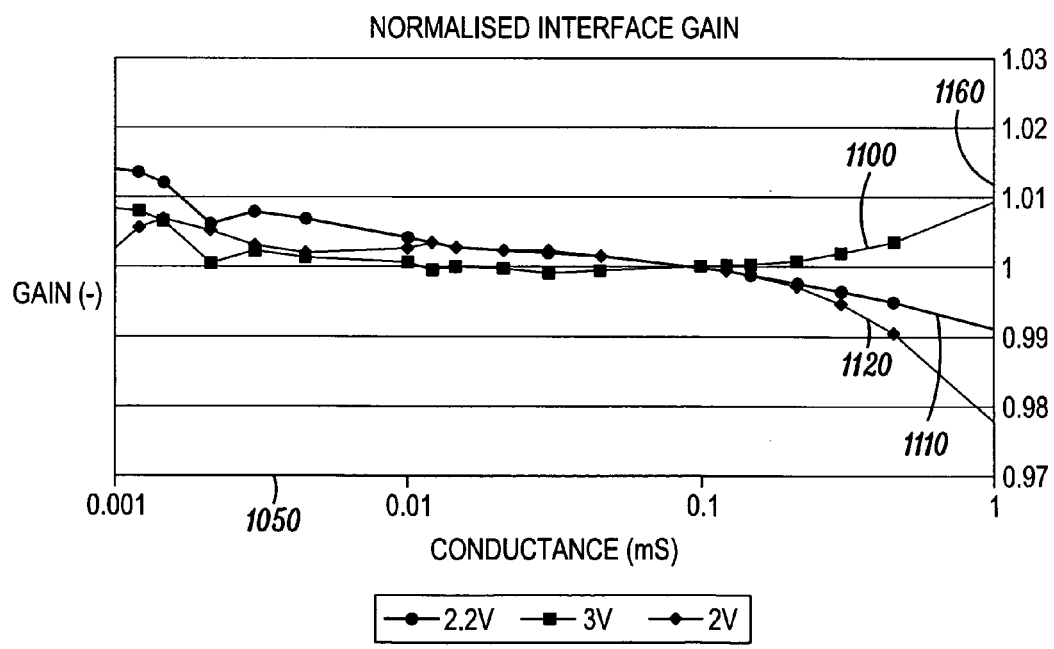
FIG. 11 is a graph of normalised gain versus conductance for a circuit similar to that shown in FIG. 9

The network N1 can be designed so as to improve the accuracy of the frequency output (f). As can be seen from FIGS. 10 and 11, the sensitivity of the circuit tends to drop off as the value of the conductance (230) tends towards 1 mS (due to the inherent impedances in the circuit and propagation delays of the gates). FIG. 10 shows the gain (1050) of the circuit of FIG. 9 in Mhz per milliSiemen, against Conductance (1060) in milliSiemens. FIG. 11 shows the gain normalised to 0.1 mS (1160) versus conductance (1050), and illustrates the linearity of the circuit across three decades of conductivity. The network N1 can be designed to boost the frequency output at low conductances and thereby compensate for reduced sensitivity at higher conductances, resulting in overall improved linearity.

According to an embodiment a circuit can be constructed with the following component values:
1. g1, g2 and g3: 74LVC04 (Low voltage CMOS)
2. $G_R$: 0.1 mS
3. C1: 680 pF plastic film or ceramic (COG/NPO)
4. C2: 1 nF plastic film or ceramic (COG/NPO)
5. N1: 47Ω in parallel with 220 pF With these component values a nominal interface gain of α=502 KHz/mS would be expected, independent of cell conductance. Therefore, with an inherent conductance (230) of 0.1 mS, the output frequency, f, with no cell connected across nodes 271 and 272 can be expected to be nominally f=50.2 KHz. The actual prototype circuit oscillated at 50.9 KHz with no cell connected.

In use, a circuit with the above component values performed well over 3 decades of conductivity (from 0.001 mS to 1 mS).

The interface gain, α in FIGS. 10 and 11, has slight sensitivity with supply voltage. FIG. 10 shows this with the three lines (1000, 1010, 1020) which correspond to a supply voltage of 3V, 2.2V and 2V respectively. FIG. 11 shows this with the three lines, normalised to 0.1 mS, (1100, 1110, 1120) which correspond to supply voltages of 3V, 2.2V and 2V, respectively. This sensitivity to supply voltage is not an important factor in practical use, since all the test measurements of the conductivity measurement method are expect to be made with a substantially constant supply voltage (for example, it can be expected that the power supply battery voltage will not change substantially throughout the time taken to record the three frequency measurements of the aforementioned method).

The test strip (260) is preferably composed of an injection moulded assembly (electrodes over moulded with the cell substrate). The reference cell (220) and the sample cell (210) have the same surface dimensions and are located one above the other in plan view. Since the length and width of each cell are the same, the ratio of cell constants is given by:

$$\frac{\theta_M}{\theta_{ref}} = \frac{d_{ref}}{d_M}$$

Where $d_{ref}$ is the depth of the reference cell (220) and $d_M$ is the depth of the sample cell (210). The depth of each cell is determined by the fluidic requirements of filling the cell through capillary action. In the sectional view shown in FIG. 8, the reference cell (220) depth $d_{ref}$ is greater than the sample cell (210) depth $d_M$ and the cell constant ratio will be greater than unity. The cells could however be of equal depth, or the sample cell depth could be greater than the reference cell depth. It is important that the sample completely fills the sample cell (210) as any air bubbles will introduce an error into the cell constant ratio.

The cells (210, 220) are sealed using a laminate on both the upper and lower surfaces of the assembly. In another embodiment the lid may comprise a thin section of the same or compatible polymer material as the cell substrate so that it can be laser welded to form a sealed device. The sample cell (210) is filled by capillary action. The reference material, if a liquid, can be filled by capillary action. Alternatively, if either a liquid or a gel it can be filled by direct dispensing, prior to sealing in manufacture. In this latter case, the capillary channels associated with the reference cell (370, 372) and the reference introduction hole (345) are not required.

The design incorporates two electrodes (240, 245) which are shared by the two cells (210, 220). The electrodes (240, 245) are manufactured from either a carbon or metal loaded polymer of suitable (high) conductivity, but could be metal or other material with suitable (high) conductivity.

A minimum exposed electrode surface area is required for each cell, in order to minimise errors caused by electrode polarisation impedance. This requirement, together with the cell depth, defines the overall size and aspect ratio of the cells. However, it is also desirable to maximise the cell base area in order to maximise heat transfer between the reference cell and the sample cell. These conflicting requirements can be reconciled to some extent if the exposed electrode area is increased without increasing the cell cross-sectional area by roughening the electrode surface finish and/or the addition of a chamfer on the edge of the electrode facing the cell.

The circuit can be constructed by known printed circuit board manufacturing and assembly techniques, or by other known electronic circuit manufacturing and assembly techniques such as hybrid construction, or can be at least partially incorporated in an Application Specific Integrated Circuit (ASIC) or a programmable logic gate device.

An example application for the present invention is the measurement of conductivity of urine. Urine has a conductivity of between 1 mS/cm and 40 mS/cm. If a reference cell (220) having a cell constant of 50 cm$^{-1}$ and a reference liquid with conductivity of 1.5 mS/cm is used, then the reference cell (220) will have a 0.03 mS conductance. The sample cell (210) having a cell constant of 150 cm$^{-1}$ will add a further 0.27 mS with urine at 40 mS/cm. Therefore, the conductance dynamic range of the circuit, required in this example, is between 0.03 mS to 0.3 mS, and an accuracy of better than + or −1% would be obtained using a circuit as provided by the present invention. The cell dimensions in this example would be 12 mm long (the dimension between the electrodes) by 4 mm wide, with $d_M$=0.2 mm and $d_{ref}$=0.6 mm (where $d_M$ is the depth of the sample cell, and $d_{ref}$ is the depth of the reference cell). In this example, the ratio of cell constants is 3. The measured temperature corrected conductivity of urine, obtainable by the present invention, can be used to correct measurements of analyte concentration in urine for urine dilution.

In another example of use, the flow of urine (which in this case will be the sample) from a patient could be used to heat the test strip (260) so that the reference assumes the same temperature as the sample.

Figure 14:
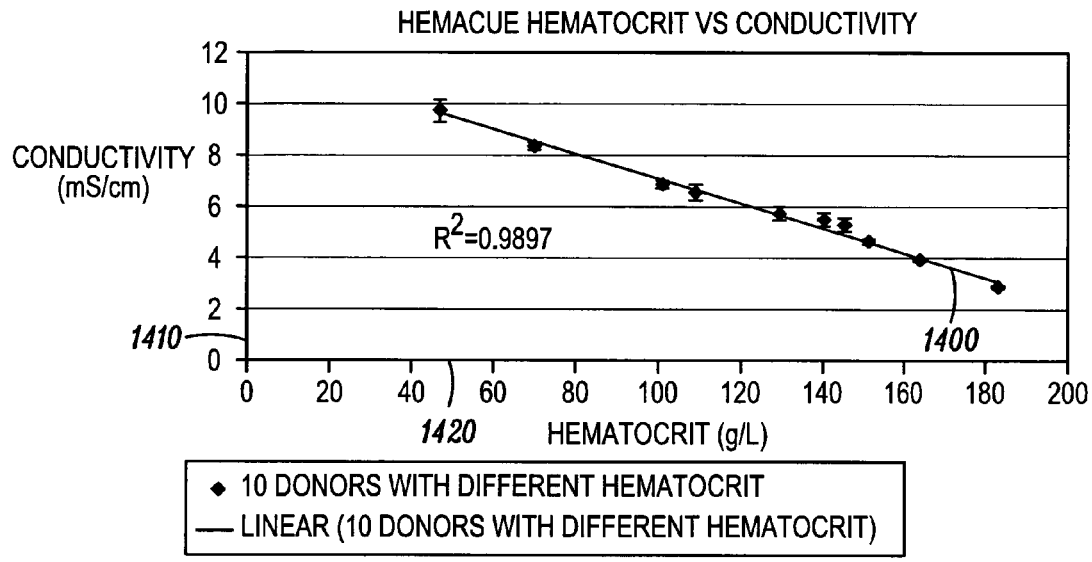
FIG. 14 is a graph of hematocrit (packed cell volume) versus blood conductivity.

Another example application for the present invention is the measurement of blood hematocrit (or packed cell volume). Measurements of conductivity were taken using the present invention, and were made on blood collected from 10 donors. Each blood sample was diluted or concentrated using its own plasma or cells to provide samples with substantially different hematocrit values. The manipulated samples were measured using a reference equipment (a Hemocue Hb201+). The Hemocue makes a measurement of the haemoglobin content of a blood sample, by lysing the blood cells using a surfactant, and making an optical absorbance measurement of the resulting solution to determine the concentration of free haemoglobin. The concentration of haemoglobin in the sample is directly proportional to the number of blood cells and therefore directly proportional to the hematocrit of the sample. Conductivity measurements were made in duplicate using the same samples and the results plotted in the graph of FIG. 14. The graph shows a substantially linear relationship (1400) between blood hematocrit (1420) and blood conductivity (1410), thus demonstrating the usefulness of conductivity measurements for determining blood hematocrit, as a simple linear equation relates conductivity to hematocrit. The "$R^2$" value shown is a measure of the goodness of fit of the fitted line to the data and has a value of 1 when the fit is perfect.

Figure 15:
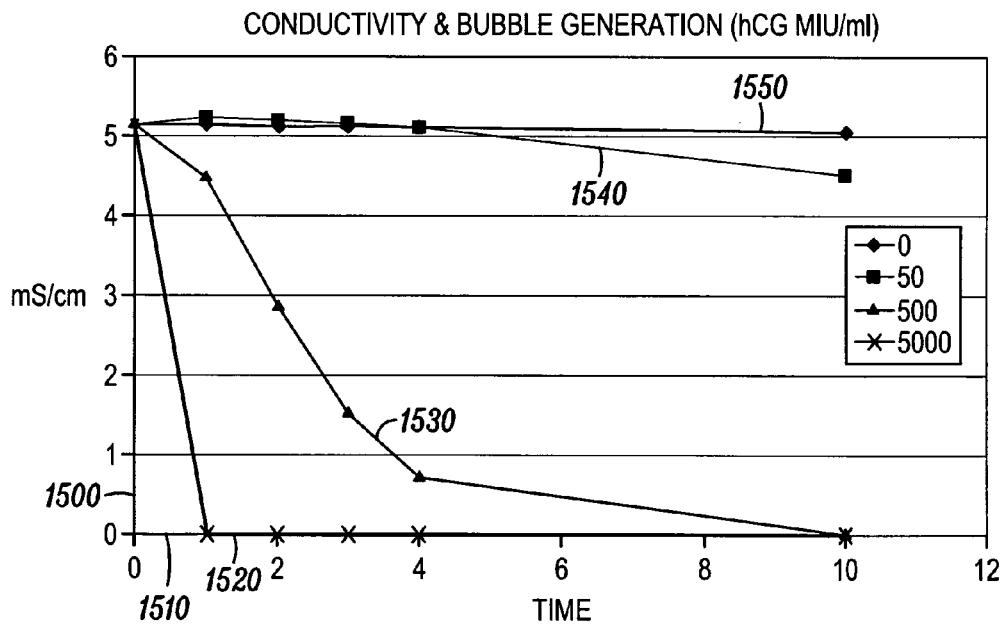
FIG. 15 is a graph of conductivity versus time for a conductivity measurement test strip where the sample container contains a reagent and bubbles are formed by the reaction of the reagent with an analyte in the sample.

A further variation on the technique presented using the method and apparatus of the present invention follows. If the sample cell is provided with a reagent, which is reactive with an analyte in the sample liquid so as to form a gas as one of its reaction products, bubbles will be formed in the sample cell at a rate proportional to the analyte concentration. As bubbles are formed, the cell conductivity will decrease because gas is generally less conductive than the sample. FIG. 15 shows a graph of time (1510) versus conductivity (1500). As can be seen, the four lines 1550, 1540, 1530 and 1520 correspond to successively greater analyte concentrations in the sample. By selecting an appropriate reagent for provision in the sample cell, it is possible to detect the concentration of a wide range of possible analytes. The reference cell could be filled with the same sample liquid, but contains no reagent so no bubbles form in it. In this way, the sample liquid serves as its own reference for temperature correction of the measured conductivity.

Existing methods for normalising urine analyte concentration for dilution use a measure of the concentration of creatinine. However, the measurement of creatinine concentration requires an enzyme cascade which is not stable and is difficult to format into a small lateral flow device.

The use of conductivity as an alternative means of concentration correction has been investigated. A 30 day study of 20 volunteers provided the raw data for statistics to develop a conversion algorithm allowing an analyte, NTx (Cross-linked N-telopeptides of type I collagen), normalised by creatinine, to be compared to the same analyte (NTx) normalised by conductivity.

$$\log\frac{NTx}{CRN} = 1.088 + 0.483\left(\log\frac{NTx}{CON}\right)$$

Additionally, a trial was conducted in which volunteers followed a low, normal or high sodium diet. Raw NTx levels appear to be higher during periods of high sodium intake. Conductivity normalisation is not adversely effected by changes in sodium intake. Dietary sodium intake appears to have little influence upon conductivity corrected NTx measurements.

Figure 16:
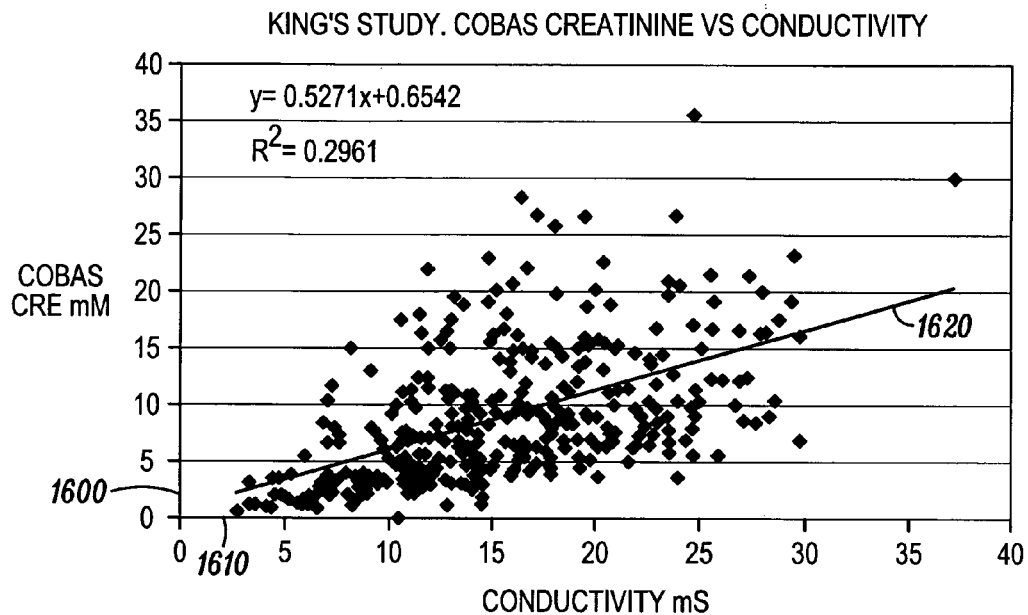
FIG. 16 is a graph of creatinine versus conductivity for urine samples from diabetic sample donors.
Figure 17:
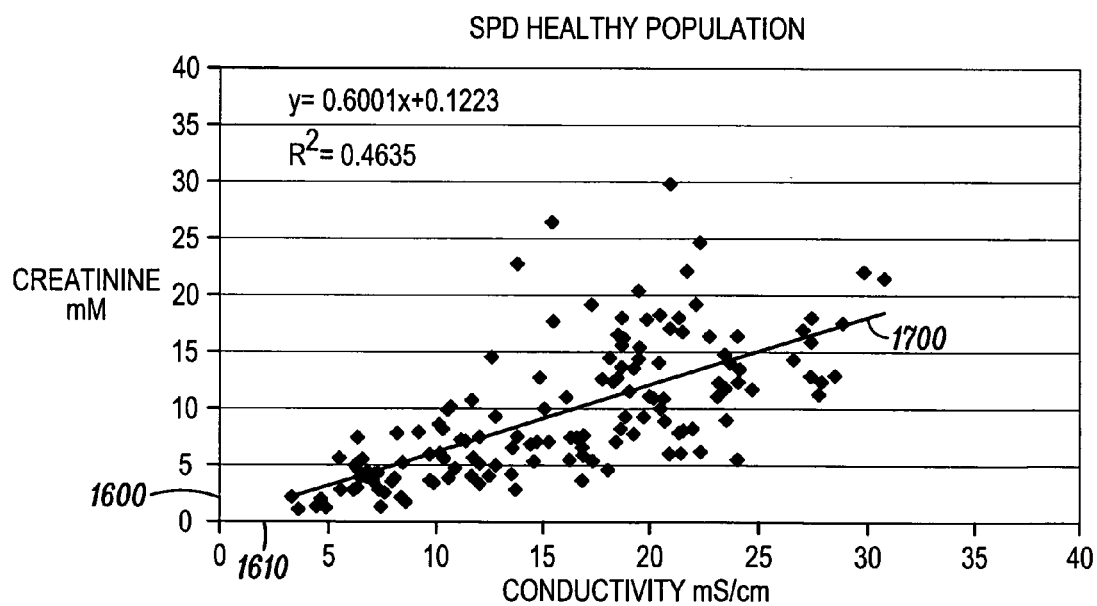
FIG. 17 is a graph of creatinine versus conductivity for urine samples from healthy sample donors.

Further, a panel of 362 randomly selected patients from the diabetic clinic were analysed. Chronic kidney disease typically effects 6-27% Type 1 diabetes, or 25-50% Type 2 diabetes patients. The results shown in FIG. 16 were obtained using urine samples from diabetic patients, whereas FIG. 17 shows results obtained using urine samples from healthy volunteers. Both Figs show creatinine concentration 1600 (y axis) versus conductivity 1610 (x axis). The line of best fit 1620 of FIG. 16 and the line of best fit 1700 of FIG. 17, when compared, show that very little difference was observed in the relationship between creatinine and conductivity dependent on diabetes incidence. Poor kidney function does not appear to have a detrimental effect on analyte (NTx in this case) measurement.

It will be noted that features of the different embodiments can be combined or juxtaposed as appropriate. For example although the sample and reference are shown as sharing electrodes in another embodiment separate electrodes may be provided and in parallel or series. Similarly although the reference and sample are shown as being separated by a membrane, they can be located in non-coincident parts of the device. The device and strip can be separate or integral.

The methods described and claimed herein can be performed in any appropriate order and are not limited to the order in which they are described.

Although the discussion above is presented in relation to samples including urine and blood, other samples such as saliva can be analysed. For example as discussed above, the device can be used to measure a conductivity per se and this value used as a direct correlation of for example % hematocrit (the volume of red blood cells in blood) since % hematocrit is directly related to the conductivity.

Alternatively the device can be used for measurement of an analyte and used to provide a corrected analyte concentration on the basis of a temperature corrected conductivity measurement, wherein the conductivity is principally a measure of the amount of dilution (i.e. water) in the sample.

In addition to urine, other bodily fluids can vary in their degree of hydration. For example serum osmolality (concentration of chemicals in blood) is controlled partly by a hormone called antidiuretic hormone (ADH). When serum osmolality increases, ADH is released. This increases the amount of water in the blood and helps restore serum osmolality to normal levels.

Hence serum osmolality varies with water concentration in urine and hence bodily hydration levels and can be analysed.

Analytes of interest include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof. Drugs of abuse include amphetamine based drugs of abuse such as MDA (3,4-methylenedioxyamphetamine), MDMA also known as "Ecstasy" (3,4-methylenedioxy-N-methylamphetamine), MDEA (3,4-methylenedioxy-N-ethylam phetamine), BDB (3,4-methylenedioxyphenyl-2-butanamine), MBDB (3,4-methylenedioxyphenyl-N-methylbutanamine), and MDPA (3,4-methylenedioxy-N-propylamphetamine); opiates such as morphine and codeine, as well as their synthetic analogues which includes heroin, hydromorphone, hydrocodone, oxycodone and oxymorphone; lysergic acid diethylamide (LSD) as well as metabolites thereof; tetrahydrocannabinol and cocaine; toxic drugs such as diazepam, nicotine, acetaminophen, caffeine, risperidone and phenobarbitol.

The assay device may comprise a binding reagent for an analyte of interest, namely a member of a binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the specific binding pair are referred to as ligand and receptor (antiligand), a binding pair member and binding pair partner, and the like. A molecule may also be a binding pair member for an aggregation of molecules; for example an antibody raised against an immune complex of a second antibody and its corresponding antigen may be considered to be a binding pair member for the immune complex.

In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogues of the original specific binding member.

Other potential applications of the device and method described herein include: professional diagnostic applications such as NTX bone marker measurement using urinary concentration correction; pre-eclampsia marker measurement in both whole blood (used as a heamatocrit volume correction) and urine (with urinary concentration correction); and improved quantitative hCG assays for high risk pregnancies such as ectopic pregnancy.

Consumer diagnostic applications include next generation fertility and contraceptive hormone monitors using urinary concentration correction, a hematocrit meter for the home testing of anaemia, an electrolyte imbalance monitor (Lithium treatment monitor etc), bubble detection in assays where bubble formation is linked to analyte presence/concentration, and kidney function tests.

Yet further, ion selective permeable membranes can be used to test, for example, for Na, K, Ca. Assays involving binding of non-conductive particles (e.g. latex) as a method of changing conductivity and giving a result can be performed and in the case of cystic fibrosis, the conductivity of baby sweat can give an indication of disease state. For erythrocyte sedimentation rate, an infection may be measured using this technology.

Other applications include a dehydration monitor using tears, sweat, saliva low volume and bacterial vaginosis (BV) assays using changes in conductivity of vaginal mucus containing BV.

The invention claimed is:
1. A conductivity measurement system comprising:
a test strip having a body, a sample container, a reference chamber, and a plurality of electrodes; and
a measurement component coupled to the electrodes and configured to obtain a plurality of conductance measurements, wherein:
the sample container and the reference chamber are separated by a coincident membrane, the coincident membrane having two opposed sides, one side in contact with the sample container and the other side in contact with the reference chamber, and
the measurement component is coupled to the sample container, the reference chamber, and the electrodes, and configured to:
based on the plurality of conductance measurements, provide a determination that a temperature of the sample container and a temperature of the reference chamber are substantially the same and,
based on the determination, derive a corrected amount or concentration of an analyte in a sample situated in the sample chamber.

2. A conductivity measurement system according to claim 1 in which the sample container and the reference chamber are arranged so as to maximize the ratio of membrane surface area to sample container volume.

3. A conductivity measurement system according to claim 1, wherein the plurality of electrodes comprises a first electrode and a second electrode, wherein the first and second electrodes are spaced apart and arranged so as to connect electrically in parallel across the reference chamber and the sample container.

4. A conductivity measurement system according to claim 1, wherein the plurality of electrodes comprises a first electrode, a second electrode and a third electrode, the first and second electrodes spaced apart and arranged so that in use they connect across the reference chamber, and the second and third electrodes arranged so that in use they connect across a sample contained in the sample container.

5. A conductivity measurement system according to claim 1 comprising a sample application zone which fluidically connects to the sample container via a capillary channel.

6. A conductivity measurement system according to claim 1 wherein the reference chamber is sealed and contains a reference liquid, gel or solid, or the reference chamber comprises an electrical component.

7. A conductivity measurement system according to claim 6 wherein the reference gel comprises potassium chloride.

8. A conductivity measurement system according to claim 1 further comprising a binding reagent for the analyte of interest.

9. A conductivity measurement system according to claim 1 wherein the electrodes have a chamfered edge in contact with the sample and/or reference, or the electrodes have surface features which increase their contact surface area with the reference and/or sample.

10. A conductivity measurement system according to claim 1 wherein the electrodes are over-molded.

11. A conductivity measurement system comprising:
a conductivity measurement test strip having a body, a sample container and a reference chamber, the sample container and the reference chamber separated by a coincident membrane, the coincident membrane having two opposed sides, one side in contact with the sample container and the other side in contact with the reference chamber;
a measurement component having a first node and a second node, wherein the test strip is configured for use with the measurement component for deriving a temperature corrected measure of electrical conductivity of a sample, and wherein the measurement component is configured to provide:
  a measurement of a first, inherent conductance of the measurement component;
  a measurement of a second conductance when a reference is connected electrically to the measurement component between the first node and the second node;
  a measurement of a third conductance when a sample is connected electrically to the measurement component; and further configured to:
    provide a determination that a temperature of the sample container and a temperature of the reference chamber are substantially the same by combining the first, second and third conductance measurements; and,
    based on the determination, derive a corrected amount or concentration of an analyte in the sample.

12. A method, comprising:
measuring a plurality of conductances using a conductivity measurement system comprising:
  a test trip having a body, a sample container and a reference chamber, the sample container and the reference chamber separated by a coincident membrane, the coincident membrane having two opposed sides, one side in contact with the sample container and the other side in contact with the reference chamber, and
  a measurement component;
based on the plurality of conductance measurements, providing a determination that a temperature of the sample container and a temperature of the reference chamber are substantially the same; and
based on the determination, deriving a corrected amount or concentration of an analyte in the sample.

13. The conductivity measurement system according to claim 1, wherein the measurement component is configured to obtain the plurality of conductance measurements, and wherein the plurality of conductance measurements comprises:
  a measurement of a first, inherent conductance of the measurement component;
  a measurement of a second conductance associated with a reference situated in the reference chamber is connected electrically to the measurement component; and
  a measurement of a third conductance associated with the reference and the sample situated in the reference chamber and the sample container, respectively; and
  wherein the measurement component provides the determination based on the measurements of the first, second and third conductances.

14. A device for deriving a corrected amount or concentration of an analyte in a sample, comprising:
  a conductivity measurement test strip having a body, a sample container, a reference chamber, the sample container and the reference chamber separated by a coincident membrane, the coincident membrane having two opposed sides, one side in contact with the sample container and the other side in contact with the reference chamber; and
  a measurement component switchably electrically coupled to the sample container and the reference chamber and configured to measure a plurality of conductances, wherein the plurality of measured conductances are used to provide a determination that a temperature of the sample container and a temperature of the reference chamber are substantially the same, and configured to, based on the determination, derive a corrected amount or concentration of an analyte in the sample.

15. The device according to claim 14, wherein the plurality of measured conductances comprise:
  a first, inherent conductance of the measurement component;
  a second conductance when a reference in the reference chamber is connected electrically to the measurement component; and
  a third conductance when a sample in the sample container is connected electrically to the measurement component, and
wherein the measurement component is configured to derive a temperature corrected measure of conductivity from the first, second and third conductance measurements in order to provide the determination.

* * * * *